United States Patent [19]

Simon et al.

[11] Patent Number: 4,457,919
[45] Date of Patent: Jul. 3, 1984

[54] METHOD OF IMPARTING IMMUNOMODULATING, ANTIVIRAL OR ANTITUMOR ACTIVITY

[75] Inventors: Lionel N. Simon, Santa Ana, Calif., Alfredo Giner-Sorolla; Riverside, Conn., and Alvin Guttag; Bethesda, Md.

[73] Assignees: Newport Pharmaceutical International, Inc., Newport Beach, Calif., Sloan-Kettering Institute, New York, N.Y.

[21] Appl. No.: 379,066

[22] Filed: May 17, 1982

Related U.S. Application Data

[62] Division of Ser. No. 130,334, Mar. 14, 1980, Pat. No. 4,340,726.

[51] Int. Cl.³ .................. A61K 31/52; C07D 473/30
[52] U.S. Cl. .............................. 424/180; 424/253; 544/265
[58] Field of Search ............... 424/180, 253; 544/277, 544/265

[56] References Cited

U.S. PATENT DOCUMENTS

| | | | |
|---|---|---|---|
| 4,151,277 | 4/1979 | Albrecht | 536/4 |
| 4,221,794 | 9/1980 | Simon et al. | 424/253 |
| 4,221,910 | 9/1980 | Giner-Sorolla | 544/265 |
| 4,321,376 | 3/1982 | Otani et al. | 544/277 |

OTHER PUBLICATIONS

Sinkula, Annual Reports in Medicinal Chemistry, vol. 10, pp. 306–316, 1975.
Yoshikawa, Bull. of The Chem. Soc. of Japan, vol. 42, pp. 3505–3508, (1969).

*Primary Examiner*—Nicholas S. Rizzo
*Attorney, Agent, or Firm*—Cushman, Darby & Cushman

[57] ABSTRACT

There are prepared compounds of the formula

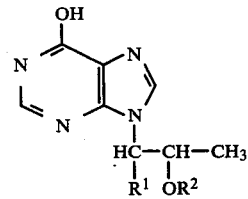

where $R^1$ is alkyl of 1 to 8 carbon atoms and $R^2$ is the ester group of an unsubstituted monocarboxylic acid, aromatic carboxylic acid, aminocarboxylic acid, unsubstituted dicarboxylic acid, phosphoric acid, or nitric acid or a glycoside or an acetaldehyde acetal. The compounds are immunomodulators, have antiviral activity and antitumor activity and also are enzyme inhibitors. The compounds can also be used to introduce the corresponding alcohol into biological systems, in some cases with enhanced potency.

6 Claims, No Drawings

METHOD OF IMPARTING IMMUNOMODULATING, ANTIVIRAL OR ANTITUMOR ACTIVITY

The invention described herein was made in the course of work under a grant or award from the Department of Health, Education and Welfare.

CROSS REFERENCE TO RELATED APPLICATIONS

This is a division of application Ser. No. 130,334 filed Mar. 14, 1980 now U.S. Pat. No. 4,340,726.

There are disclosed and claimed in Giner-Sorolla application Ser. No. 942,804, filed Sept. 15, 1978 and now U.S. Pat. No. 4,221,910, certain 9-(hydroxyalkyl) purines. These same 9-(hydroxyalkyl) purines and certain acid addition salts thereof are also disclosed in Simon et al application Ser. No. 942,802, filed Sept. 15, 1978 and now U.S. Pat. No. 4,221,909. The Simon et al application claims the acid addition salts and certain uses of the purines and the acid addition salts. The entire disclosure of the Giner-Sorolla application and the Simon et al application are hereby incorporated by reference and relied upon.

SUMMARY OF THE INVENTION

The present invention is directed to compounds of the formula

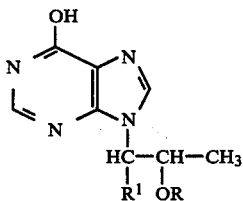

where $R^1$ is alkyl of 1 to 8 carbon atoms and $R^2$ is the ester group of an unsubstituted monocarboxylic acid, unsubstituted dicarboxylic acid, aminocarboxylic acid, aromatic carboxylic acid, phosphoric acid, or nitric acid or a glycoside or an acetaldehyde acetal. The compounds are immunomodulators, have antiviral activity and antitumor activity, especially antileukemic activity, and also are enzyme inhibitors. The compounds can also be used to introduce the corresponding alcohol into biological systems, in some cases with increased potency.

The acid portion of the ester group $R^2$ can be, for example, that of an unsubstituted aliphatic monocarboxylic acids, e.g., those having 1 to 18 carbon atoms such as formic acid, acetic acid, propionic acid, butyric acid, valeric acid, isovaleric acid, caproic acid, caprylic acid, lauric acid, palmitic acid, stearic acid, oleic acid, that of an unsubstituted aliphatic dicarboxylic acid, e.g., malonic acid, fumaric acid, maleic acid, succinic acid, glutaric acid and even carbonic acid. With the dicarboxylic acids there are usually formed the half esters, e.g., hemimalonate, hemifumarate, hemimaleate and hemisuccinate as well as the methyl carbonate and ethyl carbonate.

As aminocarboxylic acids there are employed aminoalkanoic acids such as glycine, arginine, lysine, alanine, leucine, valine, methionine.

As aromatic carboxylic acids there can be employed salicyclic acid or aralkyl carboxylic acids such as phenylacetic acid, phenyl propionic acid or phenyl alanine.

The esters of the organic acids can be prepared in conventional manner, e.g., by employing the acid anhydrides or acyl halides, e.g., acyl chlorides such as acetyl chloride. The carbonic acid esters can be prepared, for example, from chloroformic acid esters, e.g., ethyl chloroformate, methyl chloroformate or from phosgene.

The esters of inorganic acids can also be prepared in conventional manner, e.g., employing o-phenylene phosphochloridate to prepare the phosphates and the nitrates by using nitric acid.

The glycosides can be prepared of 5 to 6 carbon atom sugars such as glucose, fructose, mannose, xylose, 2-deoxyglucose, 2-deoxyribose, ribose, arabinose, galactose or rhamnose. They can be prepared by using their acetobromo sugar followed by hydrolysis of the acetyl groups. Thus there can be employed acetobromoglucose in the presence of silver carbonate in the classical Konigs-Knorr procedure (Konigs and Knorr, Sitzbayer Acad. Wis. 30, 103 (1900); Brigl and Keppler, Ber., 59, 1588 (1926) and Konigs and Knorr, Ber. 34, 974 (1901).

The acetaldehyde acetal is also prepared in conventional manner from acetaldehyde using alcoholic hydrochloric acid as a catalyst.

It is an established fact that many infectious agents, such as viruses (influenza virus, HSV, Friend Leukemia virus), bacterial and fungi cause an immune suppressed state in the host, weakening his defenses to infection by infectious agents. Most other antiviral antimetabolite substances, like AraC, cause a suppression of host immune defense mechanisms, thereby exhibiting potential to lessen the body's own natural defense mechanisms and enhance secondary infection.

An immunopotentiator or immunomodulator is any agent which either restores depressed immune function, or enhances normal immune function, or both. Immune function is defined as the development and expression of humoral (antibody-mediated) immunity, cellular (thymocyte-mediated) immunity, or macrophage and granulocyte mediated resistance. It logically includes agents acting directly on the cells involved in the expression of immune response, or on cellular or molecular mechanisms which, in turn, act to modify the function of cells involved in immune response. Augmentation of immune function may result from the action of an agent to abrogate suppressive mechanisms derived by negative-feedback influences endogenous or exogenous to the immune system. Thus, immune potentiators have diverse mechanisms of action. Despite the diversity of cell site of action and biochemical mechanism of action of immunopotentiators, their applications are essentially the same; that is, to enhance host resistance.

Applications of Immunopotentiators (1) The principal protective function of the immune system relates to resistance to invasion by pathogens, including viruses, rickettsia, mycoplasma, bacteria, fungi, and parasites of all types. Thus, improvement of immune response, particularly when depressed, would calculatedly improve resistance in infection or infestation by any of the above pathogens. An immunopotentiator alone or in combination with anti-infective therapy can be applied to any and all infectious diseases.

(2) A second protective function of the immune system is thought to be resistance to engraftment of foreign tissue, either natural as in the fetal-maternal relationship; or unnatural as performed by the transplant physician. Immunopotentiators can also be used to facilitate rejection of fetal or placental tissues or to modify or induce tolerance to grafts.

(3) A third protective function of the immune system is thought to be resistance to malignant cell development as in cancer. The use of immunopotentiators can be used in cancer treatment to enhance tumor rejection and to inhibit tumor recurrences following other forms of therapy.

(4) A fourth protective function involves the capacity to recognize foreignness and to maintain nonreactivity to self by positive suppressor mechanisms. In autoimmune and related disorders, immune reactivity directed at self antigens or exaggerated, elevated responses are apparent which are self-destructive. Immunopotentiators can be used to restore normal suppressor mechanisms, induce tolerance, or otherwise promote a normal immune response.

Each of the protective functions of the immune system can be modified by non-specific therapy with immunopotentiators alone or in combination with other agents employed to improve resistance or to kill the invading pathogen. In addition, specific resistance can be augmented by use of immunopotentiators in conjunction with some form of antigen as in a vaccine employing, for example, virus, tumor cells, etc. This use can be to induce either specific immunity or tolerance. The latter might be exemplified by use with antigen in allergy or auto-immune diseases. Use of immunopotentiators may be either therapeutic or prophylactic; the latter particularly in aging, where infection, autoimmunity, and cancer are more common. The timing of administration and routes are variable and may be critical in determining whether a positive or negative response results. Any agent capable of augmenting immune response may inhibit it depending on timing and dose; thus, under certain circumstances an immunopotentiator could be used as an immunosuppressive agent for use in allergy, auto-immunity and transplantation.

The parent alcohol when $R^1$ is hexyl is erythro-9-(2-hydroxy-3-nonyl)-hypoxanthine which has been tested under the identifying number NPT 15392. Among the compounds within the present invention are erythro-9-(2-acetoxy-3-nonyl)-hypoxanthine (identified as NPT 15458, see Example 1), erythro-9-(2-succinoxy-3-nonyl)-hypoxanthine (identified as NPT 15457, see Example 2), and erythro-9-(2-phosphate-3-nonyl)-hypoxanthine.

Other compounds within the invention include, for example, those set forth in Table 1. In Table 1, the alkyl group for $R^1$ are all n-alkyl.

TABLE 1

| $R^1$ | $R^2$ |
|---|---|
| $C_6H_{13}$ | $CH_3CH_2\overset{O}{\underset{\|}{C}}-$ |
| $C_6H_{13}$ | $CH_3CH_2CH_2\overset{O}{\underset{\|}{C}}-$ |
| $C_6H_{13}$ | $CH_3(CH_2)_{14}\overset{O}{\underset{\|}{C}}-$ |

TABLE 1-continued

| $R^1$ | $R^2$ |
|---|---|
| $C_6H_{13}$ | $CH_3(CH_2)_{16}\overset{O}{\underset{\|}{C}}-$ |
| $C_6H_{13}$ | $CH_3(CH_2)_7CH=CH(CH_2)_7\overset{O}{\underset{\|}{C}}-$ (cis) |
| $C_6H_{13}$ | $HOOCCH_2\overset{O}{\underset{\|}{C}}-$ |
| $C_6H_{13}$ | $HOOCCH=CH\overset{O}{\underset{\|}{C}}-$ (cis) |
| $C_6H_{13}$ | $HOOCCH=CH\overset{O}{\underset{\|}{C}}-$ (trans) |
| $C_6H_{13}$ | $HOOCCH_2CH_2\overset{O}{\underset{\|}{C}}O-$ |
| $C_6H_{13}$ | $HOOC(CH_2)_3\overset{O}{\underset{\|}{C}}-$ |
| $C_6H_{13}$ | $CH_2(NH_2)\overset{O}{\underset{\|}{C}}-$ |
| $C_6H_{13}$ | $CH_3CH(NH_2)\overset{O}{\underset{\|}{C}}-$ |
| $C_6H_{13}$ | $H_2NC(=NH)NHCH_2CH_2CH_2CH(NH_2)\overset{O}{\underset{\|}{C}}-$ |
| $C_6H_{13}$ | $H_2N(CH_2)_4CH(NH_2)\overset{O}{\underset{\|}{C}}-$ |
| $C_6H_{13}$ | $CH_3SCH_2CH_2CH(NH_2)\overset{O}{\underset{\|}{C}}-$ |
| $C_6H_{13}$ | $(CH_3)_2CHCH_2CH(NH_2)\overset{O}{\underset{\|}{C}}-$ |
| $C_6H_{13}$ | $C_6H_5CH_2\overset{O}{\underset{\|}{C}}-$ |
| $C_6H_{13}$ | $C_6H_5CH_2CH_2\overset{O}{\underset{\|}{C}}-$ |
| $C_6H_{13}$ | $o\text{-}HOC_6H_5\overset{O}{\underset{\|}{C}}-$ |
| $C_6H_{13}$ | $-PO_3H_2$ |
| $C_6H_{13}$ | $-NO_2$ |
| $C_6H_{13}$ | $CH_3CH\diagup^{\diagdown}$ (acetaldehyde acetal) |
| $C_6H_{13}$ | glucoside |
| $C_6H_{13}$ | riboside |
| $C_6H_{13}$ | fructoside |
| $C_6H_{13}$ | mannoside |
| $C_6H_{13}$ | rhamnoside |
| $C_6H_{13}$ | xyloside |

TABLE 1-continued

| R¹ | R² |
|---|---|
| C₆H₁₃ | galactoside |
| C₆H₁₃ | arabinoside |
| CH₃ | CH₃C(=O)— |
| CH₃ | HOOCCH₂CH₂C(=O)— |
| CH₃ | glucoside |
| CH₃ | —PO₃H₂ |
| C₂H₅ | CH₃C(=O)— |
| C₂H₅ | HOOCCH₂CH₂C(=O)— |
| C₂H₅ | glucoside |
| C₃H₇ | CH₃C(=O)— |
| C₃H₇ | HOOCCH₂CH₂C(=O)— |
| C₄H₉ | CH₃C(=O)— |
| C₅H₁₁ | CH₃C(=O)— |
| C₅H₁₁ | HOOCCH₂CH₂C(=O)— |
| C₅H₁₁ | glucoside |
| C₅H₁₁ | —PO₃H₂ |
| C₇H₁₅ | CH₃C(=O)— |
| C₇H₁₅ | HOOCCH₂CH₂C(=O)— |
| C₇H₁₅ | glucoside |
| C₈H₁₇ | CH₃C(=O)— |
| C₈H₁₇ | HOOCCH₂CH₂C(=O)— |
| C₈H₁₇ | glucoside |
| C₈H₁₇ | —PO₃H₂ |

NPT 15392 has been previously demonstrated to have antiviral immunomodulating and anti-tumor activity.

The results presented herein demonstrate that (1) novel derivatives of NPT 15392 can be prepared which (2) can be converted in biological systems to the active substance (NPT 15392), (3) lead to higher blood levels of the active substances (NPT 15392), thus enhancing the potency of NPT 15392.

The following table summarizes the chemical properties of some of the compounds of the invention.

TABLE 2

CHEMICAL PROPERTIES OF REPRESENTATIVE EXAMPLES OF CLAIMED COMPOUNDS

| | m.p. | Analysis | | $\lambda_{max}/^{A}m \times 10^3$ | | | $\lambda_{min}$ | |
|---|---|---|---|---|---|---|---|---|
| | | Theory | Found | pH 1.0 | pH 7 | pH 9.5 | pH 1 | pH 7 |
| Erythro-9-(2-Acetoxy-3-nonyl)-Hypoxanthine (NPT 15458)* | 150–151° C. | C 59.97<br>H 7.55<br>N 17.48 | 59.83<br>7.42<br>17.39 | 250/9.7 | 249.5/10.1 | 254/10.06 | 220 | 222.5 |
| Erythro-9-(2-succinoxy-3-nonyl)-Hypoxanthine (NPT-15457)** | — | — | — | 250/— | 249/— | 254/ | 222 | 223 |

*HPLC - Single UV peak on a column of 5μ spherosorb ODS. 2.1 × 250 mm using solvent of 65% methanol: 35% .05 M H₃PO₄
**Single UV peak on a column of 5μ Ultrasphere ODS 4.6 × 250 mm using a solvent of 65% Methanol: 35% 0.05 M H₃PO₄

The immunopotentiators of the invention can be employed, for example, to provide resistance to invasion by the viruses in Table A.

TABLE A

| Virus | Class | Disease |
|---|---|---|
| Arenavirus | RNA | Rift Valley Fever |
| Influenza | RNA | Influenza |
| Rhinovirus | RNA | Common Cold |
| Polio | RNA | Polio |
| Measles | RNA | Rubella |
| Newcastle Disease Virus | RNA | Newcastles Disease |
| Rotavirus | RNA | Gastroenteritis in infants |
| Hepatitis Type A | RNA | Infectious Hepatitis |
| Rabies | RNA | Rabies |
| Arbovirus | RNA | Encephalitis |
| Vaccinia | DNA | Smallpox |
| Herpes Simplex | DNA | Cold sore, Encephalitis, Venereal Disease |
| Herpes Zoster | DNA | Shingles |
| Varicella Zoster | DNA | Chicken pox |
| Adenovirus | DNA | Respiratory |
| Hepatitis Type B | DNA | Chronic Hepatitis, Severe Hepatitis |
| Hoof and Mouth Disease | DNA | Hoof and Mouth Disease |
| Machupo | DNA | Hemorrhagic Fever |

The compounds are especially useful against the RNA viruses.

The compounds and compositions of the invention are useful in treating mammals (and cells of mammals) including humans, swine, dogs, cats, cattle, horses, sheep, goats, mice, rabbits, rats, guinea pigs, hamsters, monkeys, etc.

Unless otherwise indicated, all parts and percentages are by weight.

All temperatures are in degrees centigrade unless otherwise indicated.

The compositions can comprise, consist essentially of or consist of the materials set forth and the processes can comprise, consist essentially of or consist of the steps set forth with such materials.

The compositions can be administered to the mammals by conventional techniques, e.g., orally, nasally, rectally, vaginally or parenterally. They can be employed as injectable solutions, e.g., in water, or as tables, pills, capsules, etc.

DESCRIPTION OF THE PREFERRED EMBODIMENTS

EXAMPLE 1

Synthesis of erythro-9-(2-Acetoxy-3-Nonyl)-Hypoxanthine (NPT 15458) ("ACETYL-NONYLHYPOXANTHINE")

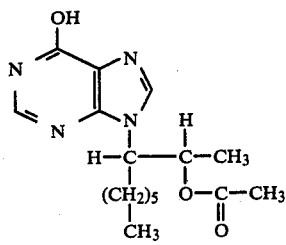

Erythro-9-(2-hydroxy-3-nonyl)hypoxanthine, NPT 15392 (2.78 g, 10 mmoles) was dissolved in pyridine (120 ml) and acetic anhydride (3 ml, 30 mmoles) added. The solution was kept at 25° C. for 24 hours. Ethanol (50 ml) was added and the solution evaporated to dryness in vacuo. This operation was repeated 4 times to eliminate the pyridine. Ether (150 ml) was added to the residue and the resulting solid collected by filtration. The precipitate was washed with ether 3 times. A white crystalline material was obtained. (2.51 g, 80%) m.p. 150°–151° C. uv$_{max}$. (H$_2$O, pH 5.5) 249 nm. A$_m$ 10.1×10$^3$, ir 1700 cm$^{-1}$(C=O).

Analyzed for C$_{16}$H$_{24}$N$_4$O$_3$ Calculated: C, 59.97; H, 7.55; N, 17.48. Found: C, 59.83; H, 7.42; N, 17.39.

Ascending chromatography (Whatman paper #1) Rf. values: n-butanol/H$_2$O/AcOH (2:1:1)=0.92; Ethanol/1M Ammonium acetate (14:6)=0.88; iso-Propanol/conc. Ammonia/H$_2$O (7:2:4)=0.90

EXAMPLE 2

Synthesis of Erythro-9-(2-Succinoxy-3-Nonyl) Hypoxanthine (Succinyl-Nonyl-Hypoxanthine) (NPT 15457)

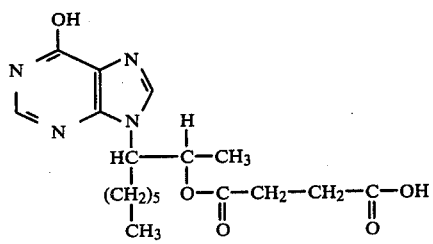

600 mg of Erythro-9-(2-Hydroxy-3-Nonyl)Hypoxanthine (NPT 15392) (2.2 mmole) and 1 gram succinic anhydride (10 mmole) were dissolved in a minimum volume of pyridine with stirring. The solution was heated gently (approx. 30° C.) with continuous stirring for 10 days.

The pyridine was removed using a rotary evaporator, and the residue was extracted into 20 ml absolute ethanol for 48 hours. This solution was centrifuged, and the supernatant purified by preparative thin layer chromatography (2 mm Silica Gel 60, N-Butanol: 2N NH$_4$OH 10:2 v/v). The band at Rf=0.17 was eluted into absolute ethanol. The purity of the product was judged from TLC and UV spectrophotometry.

Chemical Stability

The data presented in Table 3 clearly demonstrate that the esters, NPT 15458 and NPT 15457 have stability when incubated at 37° C. and neutral pH (7.0, physiological value). The fact that basic hydrolysis at pH 9.5 can convert both the Acetyl (NPT 15458) and Succinyl (NPT 15457) esters to NPT 15392 is further proof of their structure.

TABLE 3

EFFECT OF VARYING pH ON THE CHEMICAL STABILITY OF ACETOXY-NONYL-HYPOXANTHINE (NPT 15458) AND SUCCINOXY-NONYL-HYPOXANTHINE (NPT 15457)

| Compound (conc.) | | % of NPT 15392* |
|---|---|---|
| NPT 15392 (.36 μm/ml) (Control) | pH 1.0 | 100 |
| | pH 7.0 | 100 |
| | pH 9.5 | 100 |
| NPT 15457 (0.36 μm/ml) | pH 1.0 | 2 |
| | pH 7.0 | 0 |
| | pH 9.5 | 8 |
| NPT 15458 (0.36 μm/ml) | pH 1.0 | 8 |
| | pH 7.0 | 0 |
| | pH 9.5 | 28 |

*3.5 hours incubation at 37° C., determined using HPLC

Antiviral Properties

The ability of NPT 15457 and NPT 15458 to inhibit influenza virus replication was measured using the hemadsorption assay. As can be seen from Table 4, NPT 15458 prodrug, which is almost completely cleaved to NPT 15392 (active drug), has a similar capability of inhibiting virus growth as the active drug (NPT 15392). In fact, it appears as if NPT 15458 may be slightly more effective, perhaps due to a greater absorption of NPT 15458 intracellularly. The succinyl derivative, being negatively charged at pH 7.2 would not be expected to enter the cell as readily and would be less effective in this procedure.

TABLE 4

COMPARISON OF ANTIVIRAL PROPERTIES OF SUCCINOXY NONYL-HYPOXANTHINE (NPT 15457) AND ACETOXY-NONYL HYPOXANTHINE (NPT 15458) WITH NPT 15392

| | % Inhibition of Influenza Virus Growth | | | | |
|---|---|---|---|---|---|
| Drug (g/ml) | 0 | .36$^a$ | 3.6$^a$ | 10.8$^a$ | 36$^a$ |
| NPT 15392 (Control) | 0 | 20 | 30 | 42 | 73 |
| NPT 15457 | 0 | 18 | 0 | 18 | 13 |
| NPT 15458 | 0 | 26 | 40 | 80 | 88 |

$^a$Conc. in nmoles/ml.

Immunomodulating Activity

The ability of the acetoxy (NPT 15458) and succinoxy (NPT 15457) esters of NPT 15392 to modulate the immune system, both in vitro and in vivo, was measured using the following systems:
1. Mitogen induced lymphocyte proliferation using murine spleen cells (in vitro).
2. Mitogen induced lymphocyte proliferation using human peripheral blood lymphocytes (HPBL) (in vitro).
3. Enhancement of active rosette formation (in vitro).

4. Enhancement of IgM antibody formation in mice immunized with sheep red blood cells (SRBC) (in vivo).

1. The data presented in Table 5 clearly demonstrates the ability of NPT 15458 to augment PHA induced lymphocyte proliferation as measured by incorporation of tritiated thymidine. Approximately 25% increase was observed with a concentration of 50 μg/ml of NPT 15458. A similar increase was observed with 10 μg/ml of NPT 15392.

2. The data presented in Table 6 clearly demonstrates that equimolar concentrations of NPT 15457 and NPT 15458 are effectve in augmenting PHA induced lymphocyte proliferation using HPBL. This is interesting in view of the data given in Table 9, which shows that HPBL will cleave both esters to NPT 15392. NPT 15458, which is cleaved to a greater extent than NPT 15457 (see Table 9) is a more effective potentiator (Table 6, 1.48 versus 1.28) of the PHA induced transformation.

3. As can be noted from Table 7, both NPT 15457 and NPT 15458 are effective in modulating active rosette formation in HPBL. It is interesting to note that in Experiment #1, where the placebo-treated lymphocytes have a very low level of active rosettes (immunodeficient) NPT 15457 and NPT 15458 are as active as NPT 15392 in restoring the depressed immunity to normal levels. In Experiment #2, placebo-treated controls have abnormally high values for active rosettes. In this instance, NPT 15392 and NPT 15458 are able to decrease the high levels of normal values; thus, demonstrating the true immunomodulatory properties of these drugs.

4. NPT 15457 and NPT 15458 and the "active" drug, NPT 15392, were given to Balb/c mice who had been immunized with sheep red blood cells SRBC. Antibody production to SRBC was measured. It is interesting to note that NPT 15458 and NPT 15392 were very effective in modulating the production of IgM antibodies. NPT 15392, at the levels studied, produce a 46% increase in IgM production. Higher doses of NPT 15392 will cause less of an increase or decrease over control values. It is interesting to note that NPT 15458, which is converted to NPT 15392 and leads to at least 10 fold higher blood values of NPT 15392 (Table 10), produces an inhibition of IgM formation (Table 8). This is to be expected since NPT 15458 produces very high levels of NPT 15392 which are most likely inhibitory to IgM formation. The data presented in Table 8 demonstrates the immunomodulatory activity of NPT 15457 and NPT 15458. It should be noted that the effect of NPT 15457 is less than that of NPT 15458 and that less NPT 15457 is converted to NPT 15392 than NPT 15458 (Table 10).

TABLE 5
IMMUNOMODULATING PROPERTIES OF ACETOXY-NONYL-HYPOXANTHINE (NPT 15458): STIMULATION OF IN VIVO MITOGEN-INDUCED LYMPHOCYTE PROLIFERATION IN MOUSE SPLEEN CELLS

| Compound | (Conc. ng/ml) | | Cpm Incorp. −PHA | +PHA | S.I.[a] | D/C |
|---|---|---|---|---|---|---|
| 0 | | (C) | 137 | 64,647 | 471 | — |
| NPT 15392 | 10 ng/ml | (D) | 117 | 68,804 | 588 | 1.25 |
| NPT 15458 | 10 ng/ml | (D) | 153 | 66,800 | 436 | .93 |
| NPT 15458 | 50 ng/ml | (D) | 138 | 81,297 | 589 | 1.25 |

[a]S.I. equals stimulation index

TABLE 6
IMMUNOMODULATING PROPERTIES OF SUCCINOXY-NONYL-HYPOXANTHINE (NPT 15457) AND ACETOXY-NONYL-HYPOXANTHINE (NPT 15458); ENHANCEMENT OF MITOGEN-INDUCED LYMPHOCYTE PROLIFERATION IN HUMAN PERIPHERAL BLOOD LYMPHOCYTES

| Compound | Conc. n moles/ml | | Cpm Incorp. −PHA | +PHA | S.I. | D/C |
|---|---|---|---|---|---|---|
| NPT 15392* | 0 | (C) | 379 | 59,404 | 156 | — |
| | 0.036 | (D) | 297 | 59,167 | 199 | 1.27 |
| | 0.36 | (D) | 577 | 69,057 | 120 | .76 |
| | 3.6 | (D) | 381 | 67,328 | 176 | 1.128 |
| NPT 15457 | 0 | (C) | 277 | 54,015 | 195 | — |
| | 0.036 | (D) | 240 | 59,569 | 250 | 1.28 |
| | 0.36 | (D) | 228 | 59,689 | 261 | 1.33 |
| | 3.6 | (D) | 232 | 52,149 | 224 | 1.14 |
| NPT 15458 | 0 | (C) | 277 | 54,015 | 195 | — |
| | 0.036 | (D) | 214 | 59,898 | 280[a] | 1.43 |
| | 0.36 | (D) | 221 | 63,858 | 289[a] | 1.48 |
| | 3.6 | (D) | 238 | 69,055 | 290[a] | 1.48 |

*values are means of three experiments
[a]p ≤ 0.05

TABLE 7
IMMUNOMODULATING PROPERTIES OF ACETOXY-NONYL-HYPOXANTHINE (NPT 15458) AND SUCCINOXY-NONYL-HYPOXANTHINE (NPT 15457): ENHANCEMENT OF ACTIVE E-ROSETTE FORMATION

| Compound | (Conc. n moles/ml) | % Active E-Rosettes #1 | (x̄ ± S.E.) #2 |
|---|---|---|---|
| Placebo (Control) | (0) | 9.23 ± 2.9 | 34.2 ± 6.6 |
| NPT 15392 | (3.6) | 16.2 ± 1.0 | — |
| (Control) | (0.36) | — | 15.4 ± 2.9[a] |
| NPT 15457 | (3.6) | 24.8 ± 6[a] | — |
| | (0.36) | — | 33.6 ± 2.4 |
| NPT 15458 | (3.6) | 19.4 ± 1.0[a] | — |
| | (0.36) | — | 23.25 ± 1.24[a] |

[a]p ≤ 0.05 versus placebo control.

TABLE 8
IMMUNOMODULATING PROPERTIES OF ACETOXY-NONYL HYPOXANTHINE (NPT 15458) AND SUCCINOXY NONYL-HYPOXANTHINE (NPT 15457): INHIBITION OF IgM ANTIBODY PRODUCTION IN SRBC IMMUNIZED BALB/C MICE

| Expt # | Substance | (Dose i.p.) | # IgM Plaques (x̄ ± S.E.) | % of Control |
|---|---|---|---|---|
| 1 | NPT 15392 | (1.80 n moles/kg × 4) | 41 ± 4 | 146[a] |
| 2 | | (.18 n moles/kg × 4) | 68 ± 2 | 147[a] |
| 1 | NPT 15457 | (1.8 n moles/kg × 4) | 19 ± 3 | 68[a] |
| 2 | | (.18 n moles/kg × 4) | 47 ± 3 | 102 |
| 1 | NPT 15458 | (1.8 n moles/kg × 4) | 8 ± 1 | 28.5[a] |
| 2 | | (.18 n moles/g × 4) | 11 ± 1 | 23.9[a] |
| 1 | CONTROL | (placebo × 4) | 28 ± 2 | 100 |
| 2 | | (placebo × 4) | 46 ± 2 | 100 |

[a]p ≤ 0.01 compared to placebo control

Metabolic Conversion

As can be seen from Table 9, incubation of the "prodrugs", NPT 15457, and NPT 15458 with Vero Cells (African Green Monkey Kidney Cells), Liver Homogenate, and Human Peripheral Blood Lymphocytes (HPBL) leads to the formation of the "active" drug, NPT 15392. The conversion of NPT 15458 to NPT 15392 appears to occur to a greater extent than the conversion of NPT 15457 to NPT 15392.

The data in Table 10, demonstrates that both NPT 15457 and NPT 15458 can be absorbed into the blood after i.p. administration and that administration of NPT 15458 leads to almost 12 fold higher levels of NPT 15392, than if NPT 15392 is given by itself. This clearly establishes the fact that NPT 15458 and NPT 15457 can produce NPT 15392 in vivo and further at least one of these derivatives gives much higher blood levels allowing for greater activity.

TABLE 9
FORMATION OF NPT 15392 FROM ACETOXY-NONYL-HYPOXANTHINE (NPT 15458) AND SUCCINOXY-NONYL-HYPOXANTHINE (NPT 15457) BY BIOLOGICAL MEANS

| Compound | | % of NPT 15392[a] at time (hrs.) | | |
|---|---|---|---|---|
| | | 0 | 0.5 | 24 |
| NPT 15392 | Vero Cells | 100 | — | 100 |
| | Liver Homogenate | 100 | 100 | — |
| | HPBL | 100 | — | 100 |
| NPT 15457 | Vero Cells | 0 | — | 0 |
| | Liver Homogenate | 0 | 14 | — |
| | HPBL | 0 | — | 18.2 |
| NPT 15458 | Vero Cells | 0 | — | 50 |
| | Liver Homogenate | 0 | 70 | — |
| | HPBL | 0 | — | 100 |

[a]Determined using HPLC

TABLE 10
FORMATION OF NPT 15392 AFTER I.P. ADMINISTRATION TO MICE OF ACETOXY-NONYL-HYPOXANTHINE (NPT 15458) AND SUCCINOXY-NONYL-HYPOXANTHINE (NPT 15457)

| Compound Administered* | animal # | Blood Level ($\mu m/ml \times 10^3$) | | |
|---|---|---|---|---|
| | | NPT 15392 | NPT 15457 | NPT 15458 |
| NPT 15392 | 1 | 0.22 | — | — |
| | 2 | 0.68 | — | — |
| NPT 15457 | 1 | 0.47 | 1.4 | — |
| | 2 | 0.22 | 0.57 | — |
| NPT 15458 | 1 | 8.2 | — | 0 |
| | 2 | 2.7 | — | 0 |

*(360 μm/kg)

Effect of Erythro-9-(2-Acetoxy-3-Nonyl)-Hypoxanthine on Growth of Tumor (Leukemia) Cells In Vivo

| Compound | (Conc.) | % Inhibition of Growth | |
|---|---|---|---|
| | | L1210 (mouse) | 8068 (Human) |
| NPT 15458 | (10 μg/ml) | 40 | 32 |

TABLE 11
SUMMARY OF BIOLOGICAL PROPERTIES

| PROPERTY | NPT 15457 | NPT 15458 | NPT 15392 |
|---|---|---|---|
| Convertible to NPT 15392 | | | |
| Chemical | | | |
| pH 9.5 | Yes | Yes | Not Applicable |
| pH 7.0 | No | No | Not Applicable |
| Biological | | | |
| HPBL | 18 | 100 | Not Applicable |
| Liver | 14 | 70 | Not Applicable |
| Vero | 0 | 50 | Not Applicable |
| Mouse | 25 | 100 | Not Applicable |
| Biological Activity | | | |
| Antiviral (in vitro) | Very slight | Yes (88%) | Yes (73%) |
| Immunomodulating (in vitro) Lymph. Prolif. | Yes (+14–28%) | Yes (+43–48%) | Yes (+12–27%) |
| Immunomodulating (in vitro) Rosette | Yes (+166%) | Yes (+11%) | Yes (+78%) |
| Immunomodulating (in vivo) SRPC-IgM | Moderate (0–60) | Yes (−72%) | Yes (+46%) |

The following procedures were employed in order to make the determination of properties discussed above.

A. Cell Culture Methods

A. Hela or Vero Cell Propagation

1. Cell cultures in 120 cm² flasks are subcultured in monolayers in the following manner:

2. The media are poured off, and the monolayer washed two times with approximately 50 ml per wash of calcium and magnesium free phosphate buffered saline (PBS), at a pH of 7.2.

3. One ml of trypsin-EDTA solution containing 0.5 g trypsin (1:250) and 2.0 g EDTA/liter of Hanks balanced salt solution (HBSS) without Ca++ and Mg++ is added at 37° C. to each flask and dispersed over the monolayer with gentle shaking.

4. The flasks are then placed in an incubator at 37° C. for approximately 3–5 minutes, depending on the time required to dislodge the cells. Shaking by hand is required.

5. Ten ml of planting medium is added to each flask and the cells are dispersed by aspirating and expelling the suspension from the pipette. This is done ten times.

6. The contents of a series of flasks were pooled and the cells in the suspension were diluted with planting medium to 7–8.5×10⁴ cells/ml.

7. The planting medium consisted of the following composition: Minimum Essential Medium Eagles (MEM) with Earle's salts and HEPES buffer supplemented by adding the following substances as specified to 100 ml of MEM:
   10 ml of fetal calf serum (final concentration=10%)
   1 ml of 1-glutamine (200 Molar)
   1 ml of 10,000 units pencillin, 10,000 μg streptomycin and 10,000 neomycin mixture 8. The cells are subcultured into Costar tissue culture trays consisting of 24 flat bottom wells each with a 3 ml capacity per well; the cell culture suspension (1 ml) is added to each well.

9. The monolayers are used for experimentation when they reach almost confluent growth (approximately 1–2 days).

10. Separate flasks are used for maintaining the cell lines. Maintenance media consists of MEM plus supplements (see step 7) with FSC reduced to 5% final concentration.

B. Red Blood Cells

1. Whole blood is obtained by cardiac puncture from male Hartly strain guinea pigs.

2. About 10 cc of whole blood is mixed with 25 ml of Alsever's solution, and may be stored at 4° C. for up to 1 week.

3. Just prior to use, the RBC's are washed 3 times in phosphate-buffered saline (PBS), pH 7.2.

4. Each wash is accomplished by centrifuging the RBC suspension for 10 minutes at 450 g at room temperature.

5. A 0.4% v/v RBC suspension is made with Hanks balanced salt solution.

C. Egg Propagation of Viruses

A. Infection

1. Nine to ten day fertile chicken eggs are candled for viability and the placement of the air sac marked on the shell with a pencil. Questionable eggs (lack of movement or discoloration) are discarded.

2. The shell surfaces are disinfected with 70% ethanol and allowed to dry.

3. A small hole is punched through the shell with a sterile egg punch, approximately $\frac{1}{4}$" within the pencilled circle marking the air sac of each egg.

4. One-tenth ml of various virus suspension, $10^2$ to $10^3$ $EID_{50}$/ml, is inoculated through the hole with a 1 cc Tuberculine syringe at a 45° angle into the allantoic cavity. Care is taken not to injure the embryo or yolk sac.

6. One inch pieces of plastic tape are used to seal the hole and each egg is labeled with the appropriate virus, egg passage number and date.

7. Eggs are incubated at 35°–37° for 2 to 5 days, depending on the rapidity of viral growth. Incubation time and temperature are recorded along with other pertinent data for each passage.

B. Harvest of Allantoic Fluids

1. At the end of the incubation period, the eggs are chilled for 3–4 hours at 4° C. to minimize bleeding into the allantoic cavity during the virus harvesting procedure.

2. Shell surfaces are again disinfected with 70% ethanol and allowed to dry.

3. Sterile scissors are used to cut away the top of the shell along the pencilled line, and the membranes are teased off with sterile forceps.

4. The forceps are inserted gently between the embryo and shell membrane and the embryo pushed to one side, forming a "pocket" of allantoic fluid. Care is taken not to puncture the amnion (except in cases where the amnionic fluid is also to be harvested) and to minimize tearing of placental arteries.

5. A sterile, disposable 10 ml pipette with mechanized vacuum bulb is used to collect the allantoic fluid and transfer it to sterile, disposal centrifuge tube. Approximately 5–8 ml can be harvested from each egg.

6. The harvested material is centrifuged at 1200 g for 10 minutes at 4° C. Supernates are transferred to sterile tubes.

7. Samples are taken from each pool for titration and sterility testing. The remaining suspension is aliquotted into sterile 2 cc serum tubes and labeled with strain, passage number and date.

8. Aliquots are immediately frozen in liquid nitrogen and placed in storage at −70° C. in an ultrafreezer or liquid $N_2$ cryofreezer.

D. Virus Propagation in Tissue Culture

A. Infection

1. Twenty-four to 48 hour monolayer cultures of the appropriate cell type, usually in 250 cm² disposable tissue culture flasks are chosen for use when barely confluent.

2. All infection and harvesting are performed in a biological safety cabinet and only mechanical pipetting devices used. Sterile techniques are observed.

3. Twenty-five ml of maintenance medium is used to replace growth medium in cultures to be infected. Control cultures also receive 25 ml of maintenance medium.

4. The seed virus is diluted with serumfree MEM according to information supplied by the source, or from titration of previous passages, and 0.5 ml is added to each culture (except controls).

5. Cultures are incubated at 37° C. in a moist atmosphere of 5% $CO_2$, 95% air for 48–72 hours, with daily observation for the development of cytopathic effects (CPE) characteristic of each virus.

B. Harvesting

1. Cultures are removed for harvesting when the CPE reaches a score of 3 to 4+.
   - 0—No apparent cytopathic effects
   - 1+—25% of cells showing cytopathic effects
   - 2+—50% of cells showing cytopathic effects
   - 3+—75% of cells showing cytopathic effects
   - 4+—100% of cells showing cytopathic effects 2. Cultures are frozen and thawed three times to lyse and dislodge the cell layer. After thawing for the third time, the culture fluid is transferred to a sterile disposable centrifuge tube and centrifuged at 300 g for 30 minutes to remove cell debris. This virus suspension is checked for bacterial contamination.

3. Supernatants are immediately aliquotted (0.5–1 ml) into 2 cc sterile serum tubes and frozen in liquid nitrogen.

4. For titration, monolayer cultures in 24-well flat-bottom tissue culture plates are prepared and infected as follows:
   (a) Serial ten-fold dilutions of the virus are made in cold, 5% Fetal Calf Serum (FCS) maintenance medium ($10^{-1}$ to $10^{-7}$).
   (b) One ml of each dilution is added to individual wells in triplicate.
   (c) Control cultures containing only maintenance medium are included.

5. Cultures are incubated for 48 hours at 37° C. in moist 5% $CO_2$, 95° air, and the cell layers scored as previously described. $TCID_{50}$'s titer are calculated according to the Reed and Munch method of titration.

E. Hemadsorption Assay

1. Just prior to carrying out HAd assays, media are decanted from cell culture trays.

2. One mililiter of maintenance medium is added to each culture well.

3. Two series of control cultures receive maintenance medium alone.

4. Test cultures and one of the control series are immediately innoculated with 0.1 ml of diluted virus preparation. (Input titers are specified as to previous HAdFFU assays). HAdFFU is hemadsorption foci forming units.

5. The other series of controls are maintained uninfected, with MEM alone added as a blank innoculation.

6. Cultures are incubated at 37° C. for 16 to 18 hours, unless indicated otherwise.

7. After the innoculation period the media are decanted and the cells washed once with PBS at pH 7.2.

8. Five-tenths ml of the RBC suspension is added per well and the cultures maintained for 30 minutes at room temperature.

9. The RBC suspension is then decanted and the cultures are washed two to three times with PBS to remove all but specifically bound RBC's.

10. Finally, 1.0 ml of Hanks Balanced Salt Solution (HBSS) is added to each well.

11. Counting of the foci of hemadsorbed RBC's initially is performed using a Nikon inverted phase-contrast microscope with a 4X objective.

12. In all cases, a minimum of five random fields are selected per well for counting.

13. The counting of HAd foci is performed on a Bausch & Lomb Omnicon Alpha Image Analyzer.

14. The image of the microscope field is projected onto a Vidicon scanner. It is also displayed on a television screen so that the operator could detect and discount errors due to debris. Foci are detected by grayness level and image size.

15. To eliminate counting of residual unadsorbed RBC's, an oversized count module is programmed to screen out individual RBC's.

16. The statistical analysis involves analyzing the data using an analysis of variance nested design model. Source of variation may be due to treatments, wells nested within treatments, and an experimental error term due to fields within wells. Means infected cells per field and standard errors of the mean will be calculated for each well. Means and standard errors will also be calculated for each treatment by pooling the wells nested within each treatment together. The mean infected cells per field for each treatment will be compared with control using Dunnets' multiple comparison test regardless of overall F-test for treatment. (See below).

| Control | | | Treatment 1 | | |
|---|---|---|---|---|---|
| Well 1 | Well 2 | Well 3 | Well 1 | Well 2 | Well |
| F 11* | F 12 | F 13 | F' 11 | F' 12 | F' 13 |
| F 21 | F 22 | F 23 | F' 21 | F' 22 | F' 23 |
| F 31 | F 32 | F 33 | F' 31 | F' 32 | F' 33 |
| $\bar{x}_1 \pm SE_1$ | $\bar{x}_2 \pm SE_2$ | $\bar{x}_3 \pm SE_3$ | $\bar{x}_1 \pm SE_1$ | $\bar{x}_2 \pm SE_2$ | $\bar{x}_3' \pm SE_3'$ |
| Pooled | $\bar{x}_c \pm SE_c$ | | | $\bar{x}_T \pm SE_T$ | |
| | n = 9 | | | n = 9 | |

*F 11 represents field #

F. Preparation of Human Peripheral Blood Lymphocytes (HPBL)

A. Preparation of Ficoll-Hypaque Separation Medium

1. Twenty-two and a half grams of Ficoll 400 (Pharmacia, M.W. ≃400,000) are dissolved in 200 ml of distilled $H_2O$. When most of the material is in solution, the volume is then adjusted to 250 ml with distilled $H_2O$.

2. Thirty-four grams of Hypaque (sodium diatrizoate, Sterling Organics, M.W. ≃636) are dissolved in 100 ml distilled $H_2O$.

3. Solutions are then sterile filtered thorough a 0.45μ millipore filter and stored in sterile containers at 4° C. away from light.

4. Working solutions are prepared by mixing 10 ml Hypaque solution with 24 ml Ficoll solution. The mixture is warmed to 25° C. with constant stirring.

B. Separation of PBL's from Whole Blood

1. Human blood samples are obtained by veinipuncture into heparinized 20 ml-vacutainer tubes. Fifteen to twenty ml of the undiluted blood is gently layered over an equal volume of Ficoll-Hypaque solution in sterile 50 ml polycarbonate centrifuge tubes using aseptic techniques.

2. Prepared samples are centrifuged at 25° C., 400×g for 30 mins. The fuzzy white band at the interface is aseptically aspirated into a 50 ml sterile centrifuge tube with 10-20 ml RPMI-1640. The cells are washed once at 25° C. 400×g for 10 mins. at 25° C.

3. Pelleted PBL's are resuspended in 1 ml RPMI for every 8 ml whole blood originally used and counted with a Coulter counter. Concentration is adjusted with RPMI-1640 supplemented with glutamine and antibiotics. The cells are held at room temperatue until used.

G. Stimulation of HPBL with PHA and LPS

1. Ten to 40 ml of whole blood is drawn from healthy volunteers in heparinized tubes.

2. Lymphocytes are separated from the above blood using Ficoll-hypaque separation techniques.

3. Various concentration of test compound are prepared in RPMI-1640.

4. The concentration of lymphocytes are adjusted to $2 \times 10^6$/ml of RPMI-1640.

5. Lymphocytes are incubated with test compound for 90 minutes at 37° C.

6. Sheep Red Blood Cells (SRBC.s) (one to two weeks old) are washed 3 times with PBS and diluted to a final concentration of 0.5% inj RPMI-1640.

7. Reaction tubes are set up containing the following:
0.2 ml lymphocytes ($2 \times 10^6$)
0.2 ml 9% Ficoll in RPMI-1640
0.2 ml SRBC's (0.5% in RPMI-1640)

8. The above reactants are centrifuged at 200×g for 5 minutes at room temperature.

9. The sediment is then gently resuspended and a 10 l sample placed in a hemocytometer.

10. The number of rosettes are then counted using a microscope with any lymphocyte having 3 or more attached red cells being counted as a rosette.

H. E-rosette Forming Cells

A. Preparation of Mitogens

1. Lipopolysaccharide B or Phytohemagglutinin P powder is weighed and dissolved in RPMI-1640 at a concentration of 1000 μg/ml (1 mg/ml) and filter sterilized through a 0.45μ millipore filter.

2. Solutions are aliquotted (1 ml/tube) aseptically into labelled sterile cryotubes and frozen. Samples are not refrozen after partial use, but may be stored for a day or two at 4° C. Lyophilized powder is kept refrigerated at 4° C.

B. Preparation of Cultures

1. PBL's are prepared as in SOP #I-004 in serum-free RPMI-1640 supplemented with glutamine and antibiotic-antimycotic solution (GIBCO). One tenth ml per well is added to each well of 96-well microtest culture plates (CoStar Plastics) with 8-channel automatic micropipettors (Flow Labs.) fitted with sterile tips.

2. Mitogen solutions are thawed rapidly and diluted to 4 times the desired concentration with RPMI-1640.

3. Test compounds are prepared for use as per SOP #C-002, using RPMI-1640 as diluent, and diluted to 4 times the final desired concentration.

4. Fifty μl of each dilution of mitogen and/or test compound is added to 6 replicate cultures. Plain RPMI-1640 is used in the same amounts in control cultures for a total volume of 0.2 ml/well.

5. Cultures are incubated at 37° C. in a humidified 95% air, 5% $CO_2$ atmosphere (pH ≃6.0- 7.0) for 48 hours. The cells are then labelled with 0.5μCi/well ³H-TdR (Thymidine) for an additional 18 hours. the cells are harvested with a multiple automatic sample harvester (M.A.S.H.) machine. Nonadherent cells are aspirated onto glass fiber filter strips with 0.9% saline solution (10 well flushes) and the cells lysed with distilled water (20 well flushes). The strips are thoroughly air dried, residual cell deposits cut from the strips and each sample placed in 1 dram glass scintillation vials. Scintillation fluid concentrate (Scintiprep 1, Fisher Chemicals) is diluted 1:50 with scintillation grade toluene (Packard) and 1 ml added to each vial. Samples are evaluated by liquid scintillation spectroscopy and the data expressed as the means counts per minute per test group.

I. Immunoplacque Assay

A. Preparation of NPT 5392

1. A solution containing 500 µg/ml NPT 15392 is prepared by adding a preweighed amount of the drug powder to sterile PBS and sonicating the solution for 30 minutes.
2. The wavelength of GCA/McPherson double beam spectrophotometer is set to 250 nm.
3. The NPT 15392 is diluted 1:10 to 0.1 normal HCl.
4. Fifteen ml of 0.1 normal HCl is poured into beaker. This solution is used to rinse cuvettes. Both cuvettes are filled with 0.1 normal HCl and the wavelength is read. Absorbance should be within 0.001–0.005 from the zeroed value.
5. The sample cuvette is emptied and the diluted drug solution is added.
6. Absorbance is recorded and concentration is calculated as follows:

Formula: $\frac{A \text{ (absorbance)}}{11.31} \times$

Dilution factor × Atomic weight (278) = g/ml

B. Prior to Day 0

1. NPT 15392 drug solution is made by dissolving 500 g NPT 15392 per ml PBS.
2. The concentration is checked according to section A of this SOP.
3. The stock is aliquotted into 1 ml samples and stored at −20° C. for several months.
4. Solutions are thawed and diluted to desired concentration.

C. Agarose Base Plates are Made as Follows:

1. A 1.4% suspension of agarose in PBS (7 g in 500 ml) is autoclaved for 15 min.
2. Using a Cornwell syringe, 3 ml volumes of molten agarose are aseptically dispensed into Falcon #1006 petri dishes and swirled to form an even layer.
3. These plates may be stored up to one week at 4° C. prior to use. The plates are stored in an inverted position (agar on top of plate).

D. Preparation of Guinea Pig Serum

1. Ten ml of blood is removed by cardiac puncture from two to six guinea pigs and placed in a 50 ml Falcon #2070 centrifuge tube without anticoagulants.
2. These tubes are incubated for 45 min. at 37° C. for clot formation.
3. Tubes are then removed from incubator and put on ice for 30 min. to retract the clot.
4. The serum is aseptically poured off each tube, pooled, dispensed into 1 ml aliquots and stored at −70° C. until used.

E. Immunization, Day 0

1. Mice are immunized as follows: sheep blood (sheep #23) is received weekly from Hyland Labs. It is aseptically collected in two volumes of Alseviers to one volume of blood.
2. Five-tenths ml of the sheep blood in Alseviers is washed three times in sterile PBS in an IEC clinical centrifuge, setting #4 (2800 rpm) for 10 min. at room temperature.
3. The pellet is resuspended in 1:10 in sterile PBS.
4. A model Z Coulter counter is calibrated according to Coulter Instruction Manual.
5. A 1:10,000 dilution is needed for a Coulter counter cell count and is obtained by first making a 1:100 dilution in PBS and then diluting this solution 1:10 in isoton. The Coulter counter threshold is adjusted to setting #5.
6. The cell count is determined and the stock solution is diluted to $4 \times 10^7$ cells/ml. This final suspension is used for immunization.
7. Each mouse is immunized by i.v. injection into the lateral tail vein (warmed in a 50° C. water bath for veinous dilation) with 0.1 ml SRBC suspension; the final concentration of SRBC's is $4 \times 10^6$ per mouse.

F. Treatment

1. Mice are treated by i.p. injection on days 0, 1, 2 and 3. A syringe (1 cc) is fitted with a one-half inch, 26 gauge needle. The needle is introduced at a 45° angle along the right side of the linea alba. A 0.2 ml volume is given to both drug and control treated groups.
2. Drug groups are given 0.2 ml of a desired concentration NPT 15392 solution which, for a 20 g mouse, is 5 µg/ml.

G. Spleen Preparation, Day 4

1. Spleens are removed aseptically and placed individually in Falcon #2025 tissue culture tubes containing 3 ml MEM. The tubes are then stored on ice.
2. Spleens are homogenized in the same tube with a teflon pestle attached to a G. K. Heller variable speed reversible motor connected with a G. K. Heller GT-21 motor controller setting #6.
3. The homogenization time and action should be uniform from sample to sample.
4. Samples are then filtered through a 100 mesh 40 micron stainless screen into a standard tissue culture tube. The screen is rinsed with 3 ml MEM and the cell suspension is stored on ice.
5. A 1:1000 dilution is made for a Coulter counter cell count and is obtained by first making a 1:100 dilution in PBS followed by a 1:10 dilution in isoton.
6. The cell count is obtained and the stock suspension is diluted to $1 \times 10^7$ cells/ml. The Coulter counter threshold is set at 10. Red cells are lysed with three drops of Zap isoton.

H. Preparation of Top Agar (0.7%)

1. Thirty-five hundredths gram agarose and 0.53 gram MEM powder are placed into an Erlenmeyer flask. Fifty ml of distilled $H_2O$ is then added to the flask.
2. The solution is autoclaved for 15 min. at 250° F. and 15 psi. It is then placed in a 45° water bath for 5 min. The pH is adjusted to approximately 7.2 by the addition of sodium bicarbonate (0.1 ml $Na_2CO_3$).

3. One ml aliquots are dispensed into 5 ml tissue culture tubes previously placed in a water bath. Allow several extra tubes for replacement in case of plating error.

I. Preparation of 10% SRBC Solution

1. Five ml sheep blood (same batch as used for immunization) is washed three times in PBS using an IEC Clinical Standard Centrifuge, speed #4 (2800 rpm) for 10 min.

2. After the third wash, the cells are resuspended in a volume of PBS ten times the volume of the packed cells, i.e., 0.5 ml of packed SRBC's, Q.S to 5 ml with PBS.

J. Plating

Agar plates are removed from regrigerator and allowed to warm to room temperature. They are labeled in triplicate for each experimental group.

2. Agar-filled tubes are removed from the water bath. One-tenth of the 10% SRBC's and 0.1 ml spleen cell suspension are added to each agar tube. The tubes are agitated on a Vortex mixer.

3. The contents of the tubes are poured immediately into agar base plates and swirled until a smooth layer is formed. The plates are placed on a level surface until the agar solidifies.

4. The plates are incubated at 37° C. in a humidified atmosphere of 5% $CO_2$ and 95% air for 90 min.

5. Guinea pig complement (see preparation, section D) is removed from freezer, thawed at room temperature and diluted 1:10 in PBS.

6. Plates are removed from incubator and 1 ml of the diluted complement is added to each plate.

7. Plates are then incubated another 30-45 minutes at 37° C. Plates are then removed from incubator and counted using oblique light.

8. Plates can be stored at 4° C. in an inverted position and counted up to 24 hours later.

Summary of Therapeutic Uses in the Working Examples

The subject compounds of this invention have been shown to inhibit the replication of a representative sample of RNA viruses using standard tissue culture techniques. In the case of the RNA viruses, influenza virus belonging to the A sub-type was shown to be inhibited, using the hemadsorption technique. Several members of the Series NPT 15457 and NPT 15458 were shown to inhibit the replication of influenza virus at concentrations ranging from 3.6-360 n moles/ml.

Other members of the RNA class of viruses are shown in Table 6 and are responsible for the diseases specified. Of all the diseases in the world, at least 25% are known to be caused by viruses. In addition, a number of viruses have been isolated that are shown to produce tumors. Thus, antiviral agents may be expected to, themselves, have some antitumor, e.g., antileukemic properties.

The activity of one of these agents, NPT 15458 as inhibitors of the growth of abnormal lymphocytes has been determined. Notably, NPT 15458 is capable of inhibiting the proliferation of mouse leukemic lympnocytes (an L-1210 cell line) in tissue culture. A 40% inhibition of L-1210 cells was effected by NPT 15458 at 10 μg/ml.

Finally, the data presented in Table 3 demonstrates that at normal body pH's (7.2) the compounds have good chemical stability but are cleaved to the "active" substance NPT 15392 at alkaline pH. As noted in Table 9 the esters, specially NPT 15458, are cleved by incubation with animal tissues to NPT 15392. This presumably is why the subject compounds, "pro-drugs" have their indicated biological activity. In addition, the data presented in Table 10 clearly demonstrates that at least 12 fold higher blood levels of NPT 15392, the biologically "active" substance, are produced when NPT 15458 is injected i.p. than when NPT 15392 itself, is administered to mice. Further as can be noted in Table 9 Vero Cells (kidney), Liver, and HPBL all cleave the "pro-host" to the biologically active NPT 15392.

The class of substances of the invention specifically inhibit the replication of viruses, modulate (potentiate or inhibit) the immune response and inhibit the growth of leukemic lymphocytes. Based on in vitro experiments and the higher blood levels achieved with these compounds compared to NPT 15392, which demonstrate activity over a concentration range of 0.01-100 μg/ml, expected dose ranges effective in mammals are 0.0005-50 mg/kg.

Formulations

The compounds of the present invention can be fed to a mammal at a dosage of 1-1000 mg/kg of body weight and can be anticipated to be active at levels as low as 0.0005 mg/kg.

They may be administered in tablet or capsule form to humans and animals and where solubility permits in the form an aqueous syrups, or as solutions in oil, or where insoluble as a suspension. Typical pharmaceutical formulation are described below:

Capsule

NPT 15458: 0.1-500 mg
Avicel pH 101 (microcrystalline cellulose): to make 800 mg.

Suspension

Aqueous suspensions can be made with a number of suspending agents incorporated with the active drug substances. Included as suspending agents are such substances as sodium carboxymethylcellulose, Na alginate, tragacanth, Avicel RC-591 (microcrystalline cellulose), methylcellulose, Veegum, Xanthan gum. In addition to a suspending agent such substances as sweeteners, flavors, colorants, preservatives, protective colloids, and dispersants may be added.

| SYRUP FORMULATION | |
|---|---|
| NPT 15458 | 0.05-250 mg (or at a maximum level of solubility) |
| Corn Sugar | 3.25 g |
| Distilled Water | .05 g |
| FD and C Red 40 | .00175 g |
| Sodium Saccharin | .00250 g |
| Alcohol U.S.P. | .08 g |
| Methyl Paraben U.S.P | .005 g |
| Glycerin | .001 g |
| Cherry Flavor | .31225 g |
| Fruit Flavor | .00825 g |
| Distilled Water g.s. ad | 5 ml |

| TABLET FORMULATION | |
|---|---|
| NPT 15458 | 0.1-500 mg |
| Avicel pH 101 | 130 mg |
| Starch, modified | 20 mg |

| TABLET FORMULATION | |
|---|---|
| Magnesium stearate U.S.P. | 5.5 mg |
| Polyvinylpyrrolidone | 22 mg |
| Stearic acid U.S.P. | 30 mg |

What is claimed is:

1. A method of imparting immunomodulating activity, antiviral activity or antitumor activity comprising adminstering to a mannal an effective amount for such purpose of a compound of the formula:

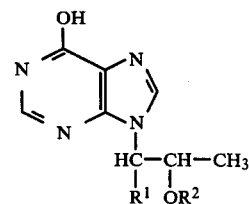

wherein $R^1$ is an n-hexyl group and $R^2$ is the ester group of formic acid, acetic acid, propionic acid or butyric acid, phenylalkanoic acid having 2 to 3 carbon atoms in the alkonic acid portions, salicyclic acid, a hemi ester of an alkaneodioic or alkenedioic acid, phosphoric acid, nitric acid, or a glycoside of a sugar having 5 to 6 atoms.

2. A method according to claim 1 wherein $R^2$ is a ester group of acetic acid.

3. A method according to claim 1 wherein $R^2$ is a hemimalonate, hemifumarate, hemimaleate or hemisuccinate.

4. A method according to claim 1 wherein $R^2$ is a hemisuccinate.

5. A method according to claim 1 wherein $R^2$ is a glucoside.

6. A method according to 1 wherein $R^2$ is the ester group of propionic acid.

* * * * *